United States Patent [19]

Nakatsukasa et al.

[11] 4,110,436
[45] Aug. 29, 1978

[54] ANTIBIOTIC A-28086 FACTOR D AND PROCESS FOR PRODUCTION THEREOF

[75] Inventors: Walter M. Nakatsukasa, Indianapolis; Robert L. Hamill, Greenwood, both of Ind.

[73] Assignee: Eli Lilly and Company, Indianapolis, Ind.

[21] Appl. No.: 762,536

[22] Filed: Jan. 26, 1977

Related U.S. Application Data

[60] Continuation-in-part of Ser. No. 657,423, Feb. 12, 1976, abandoned, which is a division of Ser. No. 569,719, Apr. 21, 1975, abandoned.

[51] Int. Cl.$^2$ ............................................. A61K 35/00
[52] U.S. Cl. ................................................... 424/122
[58] Field of Search .......................................... 424/122

[56] References Cited

U.S. PATENT DOCUMENTS

| 3,794,732 | 2/1974 | Raun | 424/283 |
| 3,839,557 | 10/1974 | Raun | 424/115 |

OTHER PUBLICATIONS

Derwent Farm Doc. #58498, U-BCD, Abstracting DJ-2253031-Q, Published 2-9-73.

*Primary Examiner*—Jerome D. Goldberg
*Attorney, Agent, or Firm*—Nancy J. Harrison; Arthur R. Whale

[57] ABSTRACT

Newly-discovered antibiotic A-28086 factor D, produced by submerged aerobic fermentation of *Streptomyces aureofaciens* NRRL 8092, is an antibacterial and anticoccidial agent and also increases feed-utilization efficiency in ruminant animals.

10 Claims, 3 Drawing Figures

ANTIBIOTIC A-28086 FACTOR D AND PROCESS FOR PRODUCTION THEREOF

CROSS-REFERENCE TO RELATED APPLICATION

This is a continuation-in-part of application Ser. No. 657,423, filed Feb. 12, 1976, now abandoned, which in turn is a division of application Ser. No. 569,719, filed Apr. 21, 1975, now abandoned.

BACKGROUND OF THE INVENTION

Antibiotic A-28086 factor D is a newly-discovered member of a group of polyether antibiotics. Examples of members of this group include the earlier-discovered antibiotic A-28086 factors A and B (see copending U.S. patent application Ser. No. 477,954, filed on June 10, 1974); monensin (U.S. Pat. No. 3,501,568); dianemycin [R. L. Hamill, M. M. Hoehn, G. E. Pittenger, J. Chamberlin, and M. Gorman, *J. Antibiotics* 22, 161 (1969)]; nigericin [L. K. Steinrauf, Mary Pinkerton, and J. W. Chamberlin, *Biochem. Biophys. Res. Comm.* 33, 29 (1968)];and salinomycin (U.S. Pat. No. 3,857,948).

SUMMARY OF THE INVENTION

This invention relates to a newly-discovered antibiotic substance which is arbitrarily designated herein as antibiotic A-28086 factor D. Antibiotic A-28086 factor D and the earlier-described A-28086 factors A and B are coproduced by culturing a new strain of the organism *Streptomyces aureofaciens* Duggar, NRRL 8092. The $C_2$-$C_6$-acyl ester derivatives of A-28086 factor D and the physiologically-acceptable salts of said ester derivatives and of A-28086 factor D are also part of this invention.

Antibiotic A-28086 factor D is produced together with factors A and B by culturing the novel strain of *Streptomyces aureofaciens* NRRL 8092 under submerged aerobic fermentation conditions until a substantial level of antibiotic activity is produced. The coproduced factors A, B, and D are extracted from the fermentation broth and from the mycelium with polar organic solvents. The co-produced factors are separated as a mixture by concentrating the polar organic solvents, adding the concentrates to excesses of petroleum ether to precipitate impurities, filtering, and evaporating the filtrates to obtain A-28086 antibiotic complex. It should be noted that the term "antibiotic complex" as used in the fermentation art and in this specification does not refer to a chemical complex, but to a mixture of co-produced individual antibiotic factors. As will be recognized by those familiar with antibiotic production by fermentation, the ratio of individual factors produced in an antibiotic complex will vary, depending on the fermentation conditions used. The A-28086 antibiotic complex is further purified and is separated into individual factors A, B, and D by a series of chromatographic procedures.

Antibiotic A-28086 factor D of this invention inhibits the growth of organisms which are pathogenic to animal and plant life. In one aspect of this inhibitory activity, antibiotic A-28086 factor D is an anticoccidial agent. In addition, antibiotic A-28086 factor D is an antibacterial agent and increases feed-utilization efficiency in ruminant animals.

This invention also relates to another method of preparing the earlier-discovered antibiotic A-28086 factor A.

DESCRIPTION OF THE DRAWING

The following infrared absorption spectra in chloroform are presented in the drawings.

DETAILED DESCRIPTION OF THE INVENTION

Figure 1:
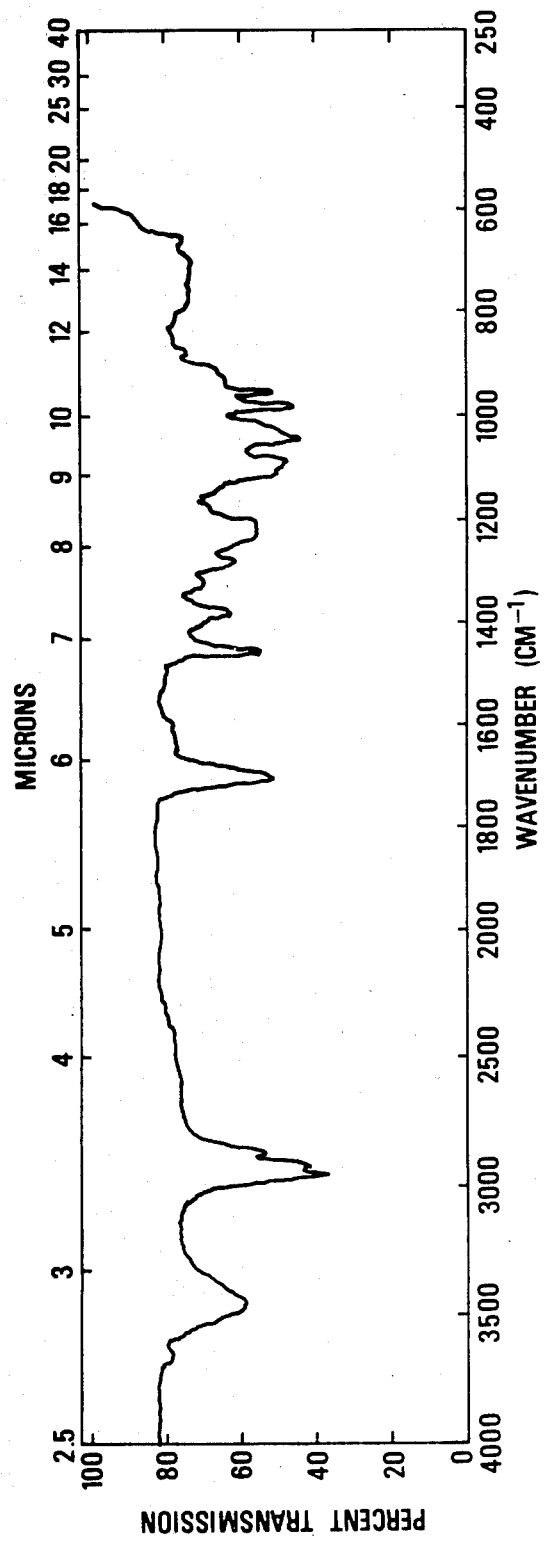
FIG. 1 — Antibiotic A-28086 factor D

Newly-discovered antibiotic A-28086 factor D of this invention is structurally related to the earlier-discovered factors A and B. A-28086 factors A, B, and D are coproduced during the fermentation and are obtained as a mixture. The factors are separated from each other, and factor D is isolated as an individual compound as hereinafter described.

Antibiotic A-28086 factors A and B are described in detail in a copending U.S. patent application of Berg et al. titled ANTIBIOTIC A-28086 AND PROCESS FOR PRODUCTION THEREOF, Ser. No. 569,740, filing date Apr. 21, 1975.

The following paragraphs describe the physical and chemical properties of newly-discovered antibiotic A-28086 factor D.

Antibiotic A-28086 factor D is a white crystalline material (from water-acetone) with a melting point of about 96°-98° C. A-28086 factor D has an apparent molecular weight of 778, as determined by high-resolution mass spectrometry.

The elemental composition of the peak in the mass spectrum of the sodium salt of A-28086 factor D was observed to be 800.5050 (Calcd. for $C_{44}H_{73}O_{11}Na$ = 800.5050). In the mass spectrum of A-28086 factor D free acid, a small peak at 778 and a larger peak at 760.5117 (calcd. for $C_{44}H_{72}O_{10}$ = 760.5125) were observed. The m/e 760 in the mass spectrum of the free acid results from the loss of water from the molecular ion. The molecular-ion composition of A-28086 factor D free acid is, therefore, $C_{44}H_{74}O_{11}$.

The empirical formula proposed for A-28086 factor D is $C_{44}H_{74}O_{11}$. Elemental analysis of factor D gave the following percentage composition: carbon, 67.59 percent; hydrogen, 9.38 percent; oxygen, 22.77 percent.

The theoretical percentage composition for $C_{44}H_{74}O_{11}$ is: carbon, 67.87 percent; hydrogen; 9.51 percent; oxygen, 22.77 percent.

The infrared absorption spectrum of A-28086 factor D in chloroform is presented in the accompanying drawing. The following absorption maxima are observed: 2.89, 3.39, 3.43, 3.50, 5.88, 6.90, 7.27, 7.60, 7.84, 9.00, 9.26, 9.62, 10.31, 10.58, 11.10, and 11.49 microns.

A-28086 factor D in 95 percent aqueous ethanol shows no ultraviolet absorption.

The nuclear magnetic resonance spectrum of A-28086 factor D in deuterochloroform showed the following characteristics: δ 6.00, 4.20, 4.10, 4.00, 3.98, 3.92, 3.86, 3.83, 3.79, 3.67, 3.64, 3.57, 3.54, 2.88, 2.81, 2.71, 2.62, 2.58, 2.48, 2.43, 2.37, 2.29, 2.21, 2.15, 2.10, 2.04, 1.97, 1.89, 1.83, 1.76, 1.68, 1.61, 1.58, 1.55, 1.47, 1.39, 1.30, 1.25, 1.18, 0.95, 0.90, 0.88, 0.84, 0.74, and 0.68 ppm.

Antibiotic A-28086 factor D, crystallized from acetone-water, has the following characteristic X-ray powder-diffraction pattern ($Cu^{++}$ radiation, 1.5405λ, nickel filter, d=interplanar spacing in angstroms):

| d | Relative Intensity |
| --- | --- |
| 12.40 | 100 |
| 10.20 | 70 |
| 8.85 | 90 |
| 7.80 | 30 |
| 6.80 | 10 |
| 6.30 | 100 |
| 5.70 | 20 |
| 5.35 | 20 |
| 5.10 | 20 |
| 4.90 | 10 |
| 4.65 | 20 |
| 4.45 | 40 |
| 4.20 | 30 |
| 3.30 | 10 |
| 3.15 | 10 |
| 2.99 | 05 |
| 2.77 | 05 |
| 2.28 | 05 |

The specific rotation of antibiotic A-28086 factor D is −56° (c=0.1, methanol), when determined at a temperature of 25° C.

Electrometric titration of A-28086 factor D in 80 percent aqueous dimethylformamide indicated the presence of a titratable group with a $pK_a$ value of 8.67.

Antibiotic A-28086 factor D is soluble in a variety of organic solvents such as methanol, ethanol, dimethylformamide, dimethyl sulfoxide, ethyl acetate, chloroform, acetone and benzene. A-28086 factor D is only slightly soluble in nonpolar organic solvents such as hexane and is insoluble in water.

Antibiotic A-28086 factor D has an acid function capable of forming salts and ester derivatives and at least one hydroxyl group capable of esterification.

Based on the physical characteristics hereinabove recited, a structure for antibiotic A-28086 factor D can be proposed. Since the structure determination is merely postulated, however, it is to be understood that the structure presented herein represents merely a working hypothesis. The tentative structure for A-28086 factor D is shown in Formula I:

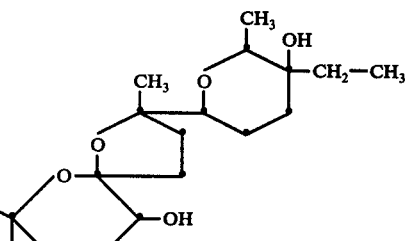
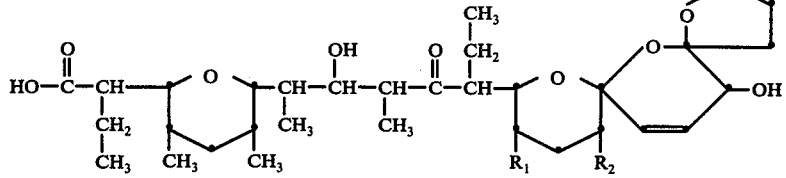

wherein
either: $R_1 = CH_3$ and $R_2 = C_2H_5$
or: $R_1 = C_2H_5$ and $R_2 = CH_3$ The $R_f$ values of antibiotic A-28086 factor D in various paper-chromatographic systems, using *Bacillus subtilis* ATCC 6633 as a detection organism, are given in Table I. The $R_f$ values of A-28086 factors A and B in these systems are included for reference purposes.

TABLE I

| $R_f$ Value | | | |
| --- | --- | --- | --- |
| Factor D | Factor A | Factor B | Solvent System |
| 0.10 | 0.11 | 0.09 | Water saturated with methyl isobutyl ketone (MIBK) |
| 0.26 | 0.41 | 0.16 | Water saturated with MIBK plus 2% p-toluenesulfonic acid and 1% piperidine |
| 0.36 | 0.54 | 0.46 | Water:methanol:acetone (12:3:1)- adjusted to pH 10.5 with NH₄OH and then lowered to pH 7.5 with H₃PO₄ |
| 0.29 | 0.48 | 0.36 | 1% MIBK, 0.5% NH₄OH in water |
| 0.25 | 0.15 | 0.33 | 17.4 g. K₂HPO₄, 30 ml. ethanol per liter of water |
| 0.26 | 0.24 | 0.51 | Benzene saturated with water |
| 0.09 | 0.24 | 0.11 | Water |
| 0.64 | 0.75 | 0.61 | Water:MIBK:ethyl acetate (98:1:1) |

In Table II are given the $R_f$ values for antibiotic A-28086 factor D in two thin-layer-chromatographic systems on silica gel (precoated plates, E. Merck, Darmstadt, F-254, layer thickness 0.25 mm), again using *B. subtilis* ATCC 6633 as a detection organism.

TABLE II

| $R_f$ Values | | | |
| --- | --- | --- | --- |
| Factor D | Factor A | Factor B | Solvent System |
| 0.26 | 0.24 | 0.42 | Benzene-ethyl acetate (3:2) |
| 0.66 | 0.54 | 0.34 | Ethyl acetate-diethylamine (95:5) |

A-28086 factor D forms acyl ester derivatives. Esterification occurs at one of the hydroxyl groups of A-28086 factor D upon treatment with a $C_2$–$C_6$-acid anhydride or acid chloride. Such esters are typically prepared by reacting A-28086 factor D with, for example, the corresponding acid anhydride at room temperature. These ester derivatives are also useful as antibiotics and as agents which increase feed-utilization efficiency.

The following paragraphs describe characteristics of typical A-28086 factor D acyl-ester derivatives.

A-28086 factor D acetyl ester derivative, a white solid, has a molecular weight of about 820, as determined by electron-impact mass spectrometry, an empirical formula of $C_{46}H_{76}O_{12}$, and an elemental composition of approximately 67.32 percent carbon, 9.27 percent hydrogen, and 23.41 percent oxygen.

Figure 2:
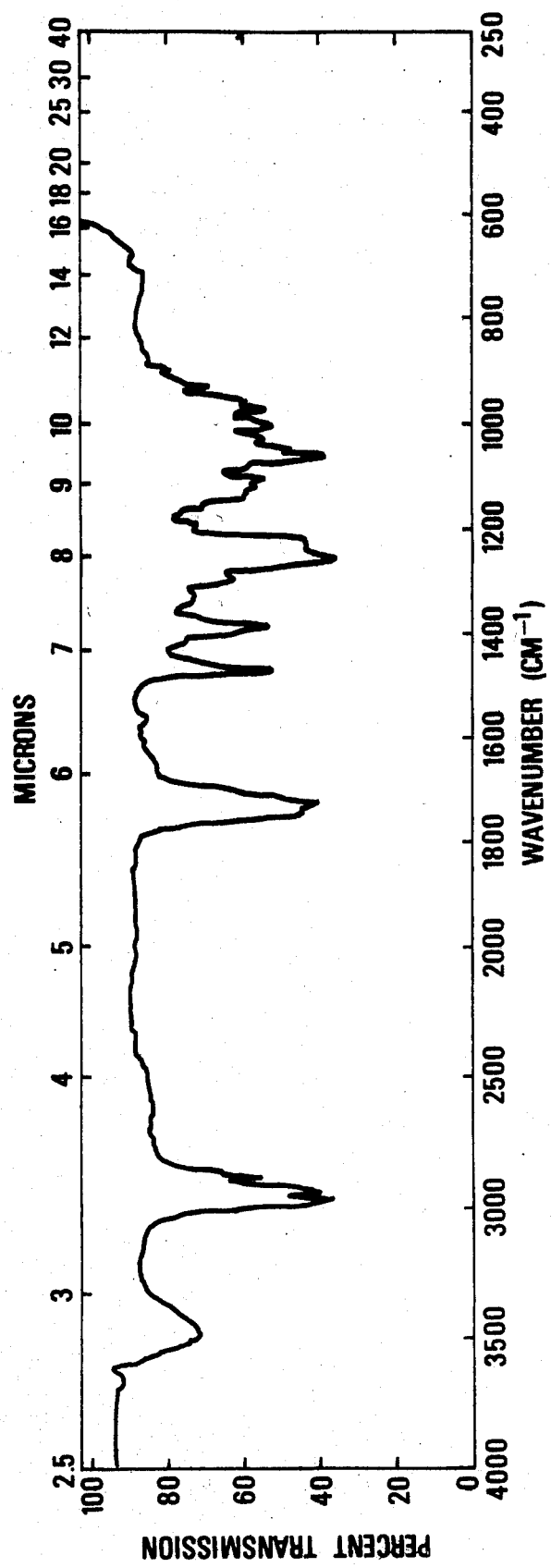
FIG. 2 — Antibiotic A-28086 factor D acetyl ester derivative

The infrared absorption spectrum of A-28086 factor D acetyl ester derivative in chloroform is shown in FIG. 2 of the accompanying drawings. The following absorption maxima are observed: 3490, 2970, 2935, 2880, 2860 (shoulder), 1745, 1725, 1565, 1470, 1385, 1330, 1295, 1255, 1190, 1155 (shoulder), 1130, 1115, 1100, 1060, 1040 (shoulder), 1020, 1000, 970, 950, 925, and 895 wavenumbers (cm⁻¹).

A-28086 factor D n-butyryl ester derivative, a white solid, has a molecular weight of about 848, as determined by electron-impact mass spectrometry, an empirical formula of $C_{48}H_{80}O_{12}$, and an elemental composition of approximately 67.93 percent carbon, 9.43 percent hydrogen, and 22.44 percent oxygen.

Figure 3:
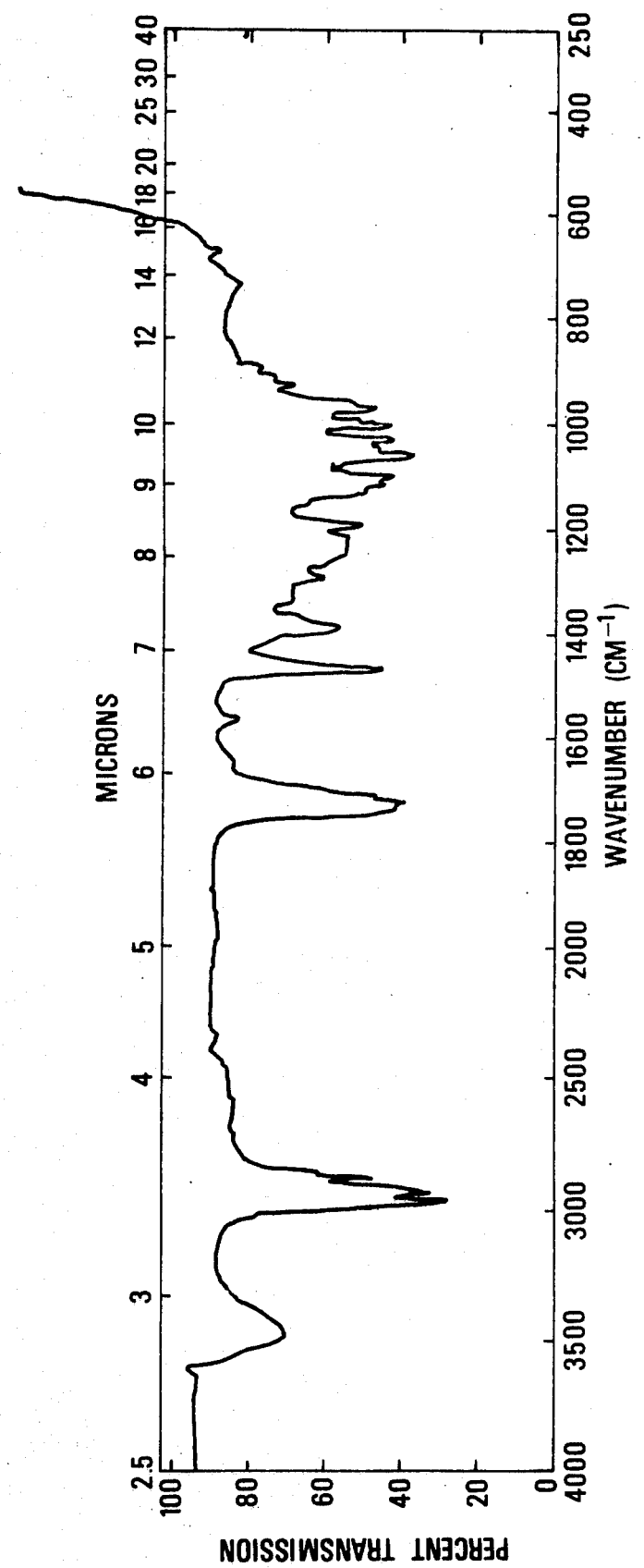
FIG. 3 — Antibiotic A-28086 factor D n-butyryl ester derivative

The infrared absorption spectrum of A-28086 factor D n-butyryl ester derivative in chloroform is shown in FIG. 3 of the accompanying drawings. The following absorption maxima are observed: 3480, 2970, 2940, 2880, 2860 (shoulder), 1740, 1725, 1710 (shoulder), 1565, 1470, 1390, 1330, 1292, 1190, 1130, 1115, 1100, 1060, 1028, 1000, 970, 955 (shoulder), 920, 910 and 890 wavenumbers $(cm^{-1})$.

A-28086 factor D can be distinguished from its acetyl and n-butyryl ester derivatives by silica-gel thin-layer chromatography (TLC) using an ethyl acetate solvent system. A vanillin spray reagent (3% vanillin in methanol + 0.5 ml. conc $H_2SO_4$ per 100 ml. of solution) can be used for detection. A-28086 factor D and its acetyl and n-butyryl ester derivatives have the following approximate $R_f$ values on TLC in this system:

|  | $R_f$ Value |
|---|---|
| A-28086 factor D | 0.29 |
| A-28086 factor D acetyl ester derivative | 0.54 |
| A-28086 factor D n-butyryl ester derivative | 0.61 |

Antibiotic A-28086 factor D and its $C_2$–$C_6$-acyl ester derivatives are capable of forming salts. The physiologically-acceptable alkali-metal, alkaline-earth-metal and amine salts of antibiotic A-28086 factor D and of the $C_2$–$C_6$-acyl-ester derivatives of A-28086 factor D are also part of this invention.

To simplify discussions of utility, the term "A-28086-factor-D compound" is used to refer to A-28086 factor D, a $C_2$–$C_6$-acyl-ester derivative of factor D or a physiologically-acceptable salt of A-28086 factor D or of a $C_2$–$C_6$-acyl-ester derivative of factor D as above defined.

"Physiologically-acceptable" salts are salts which are also pharmaceutically acceptable, that is, salts in which the toxicity of the compound as a whole toward warm-blooded animals is not increased relative to the non-salt form. Representative and suitable alkali-metal and alkaline-earth-metal salts include the sodium, potassium, lithium, cesium, rubidium, barium, calcium, and magnesium salts. Suitable amine salts include the ammonium and the primary, secondary and tertiary $C_1$–$C_4$-alkylammonium and hydroxy-$C_2$–$C_4$-alkylammonium salts. Illustrative amine salts include those formed by reaction with ammonium hydroxide, methylamine, sec-butylamine, isopropylamine, diethylamine, di-isopropylamine, ethanolamine, triethylamine, 3-amino-1-propanol, and the like.

The alkali-metal and alkaline-earth-metal cationic salts of A-28086 factor D and of the $C_2$–$C_6$-acyl ester derivatives of factor D are prepared according to procedures commonly employed for the preparation of cationic salts. For example, the free-acid form of the antibiotic factor or ester derivative is dissolved in a suitable solvent such as warm methanol or ethanol; a solution containing the stoichiometric quantity of the desired inorganic base in aqueous methanol is added to this solution. The salt thus formed can be isolated by routine methods, such as filtration or evaporation of the solvent.

The salts formed with organic amines can be prepared in a similar manner. For example, the gaseous or liquid amine can be added to a solution of the antibiotic factor in a suitable solvent such as acetone, and the solvent and excess amine can be removed by evaporation.

It is well known in the veterinary pharmaceutical art that the form of an antibiotic is not significant when treating an animal with the antibiotic. In most cases, conditions within the animal change the drug to forms other than the form in which it was administered. The salt form in which it may be administered is, therefore, insignificant to the method of treatment. The salt form may, however, be chosen for reasons of economics, convenience, and toxicity.

The novel antibiotic factor of this invention is produced by culturing an A-28086-factor-D-producing strain of Streptomyces aureofaciens under submerged aerobic conditions in a suitable culture medium until substantial antibiotic activity is produced. A-28086 factor D is recovered from the fermentation medium by the use of a combination of isolation and purification procedures. The general methods of the isolation and purification procedures used are well known.

The new organism especially useful for the preparation of antibiotic A-28086 factor D was derived by a series of natural selections followed by chemical mutation from the strain of Streptomyces aureofaciens NRRL 5758 previously deposited for the production of A-28086 factors A and B in copending application Ser. No. 477,954, filed on June 10, 1974. After the discovery of A-28086 factor D produced by S. aureofaciens NRRL 8092, it was recognized that S. aureofaciens NRRL 5758 also produces A-28086 factor D as a minor factor.

The new A-28086-producing strain NRRL 8092 which is especially useful for the production of A-28086 factor D is also classified as a strain of Streptomyces aureofaciens Duggar, as described by E. B. Shirling and D. Gottlieb in "Cooperative Description of Type Cultures of Streptomyces. III. Additional Species Descriptions from First and Second Studies," *Intern. Bull Systematic Bacteriol.* 18, 279–392 (1968). This classification is based on methods recommended for the International Streptomyces Project [E. B. Shirling and D. Gottlieb, "Methods for Characterization of Streptomyces species," *Intern. Bull. Systematic Bacteriol.* 16, 313–340 (1966)] along with certain supplementary tests. Color names were assigned according to the ISCC-NBS method (K. L. Kelly and D. B. Judd, "The ISCC-NBS Method of Designating Color and a Dictionary of Color Names," U.S. Dept. of Commerce, Circ. 553, 1955, Washington, D.C.). Figures in parentheses refer to the Tresner and Backus color series [Tresner, H. D. and S. J. Backus, "System of Color Wheels for Streptomyces Taxonomy," *Appl. Microbiol.* 11, 335–338 (1963)]; color tab designations are underlined. The Maerz and Paul color blocks (A. Maerz and M. R. Paul, "Dictionary of Color," McGraw-Hill Book Co., Inc., New York, N. Y., 1950) are enclosed in brackets. Cultures were grown at 30° C. for 14 days unless otherwise noted.

CHARACTERIZATION OF A-28086-PRODUCING STRAIN NRRL 8092

Morphology

On medium ISP No. 7 (tyrosine agar) the culture produces occasional hooks, but mainly produces short, straight sporophores. Spore chains are less than 10 spores per chain, usually four–seven spores per chain.

Short straight spore chains were observed in the following media: ISP No. 3, Czapek's-solution agar and ISP No. 5. Abundant coremia were observed on Emerson's agar. Electron microscope observations were made on tyrosine agar (ISP No. 7) and glucose-asparagine agar. Spores are smooth and range in size from 1.2 to 2.0μ in length and about 1.0μ in diameter. The average spore size is 1.6μ × 1.0μ.

| Medium | Cultural Characteristics on Various Media |
| --- | --- |
| | Characteristics |
| ISP No. 2 (yeast extract-malt extract) | Growth-fair; reverse light yellow brown [12H8]; fair aerial mycelium; poor sporulation; aerial pale grey [11A1]; no soluble pigment. |
| ISP No. 3 (Oatmeal) | Growth-sparse; reverse hyaline; no aerial mycelium; no soluble pigment. |
| ISP No. 4 (inorganic salts-starch agar) | Growth-moderate; reverse greyish yellow [11B2]; scant aerial mycelium and sporulation; aerial pale yellow grey [10A1]; no soluble pigment. |
| ISP No. 5 (glycerol-asparagine agar) | Growth-moderate; reverse pale yellow [10F2]; fair aerial mycelium; scant sporulation; aerial white [10A1]; no soluble pigment. |
| Tomato paste-oatmeal agar | Growth-moderate; reverse greyish green-yellow; aerial mycelium fair; moderate sporulation, light pale gray [53A2]; no soluble pigment. |
| Glycerol-glycine agar | Growth-abundant; reverse greyish yellow [11E4]; moderate aerial mycelium, white [10A1]; no sporulation; no soluble pigment. |
| Glucose-asparagine agar | Growth-moderate; reverse pale yellow [10F2]; moderate aerial mycelium and sporulation, white [10A1]; no soluble pigment. |
| Nutrient agar | Growth-sparse; reverse pale yellow [10B2]; no aerial mycelium; no soluble pigment. |
| Bennett's agar | Growth-fair; reverse medium yellow pink [11A7]; very scant aerial mycelium; no sporulation; no soluble pigment. |
| Calcium malate agar | Growth-very scant, hyaline; no aerial mycelium, no soluble pigment. |
| Czapek's solution agar | Growth-very scant; reverse hyaline; no aerial mycelium; no soluble pigment. |
| Emerson's agar | Growth-moderate; reverse greyish yellow [11I5]; spotty aerial mycelium; no sporulation; no soluble pigment. |
| Tyrosine agar | Growth-moderate; reverse light yellow brown [12H6]; moderate aerial mycelium, light pale grey margin [53A2], center near white, and moderate sporulation; no soluble pigment. |
| Tryptone-yeast agar | Growth-very scant, hyaline; no aerial mycelium; no soluble pigment. |

Organism NRRL 8092 was studied for selected physiological properties in accordance with standard procedures. The properties observed and characteristics found were as follows:

| Property Observed | Characteristic |
| --- | --- |
| Action on milk | peptonized (90%); pale-yellow growth ring, cleared area pale yellow-pH reaction 4.6 |
| Nitrate reduction | Positive |
| Nutrient gelatin | 50% hydrolyzed at 14 days |
| Melanin pigment | |

| Property Observed | Characteristic |
| --- | --- |
| production on: | |
| Tyrosine-agar slants | Very weakly positive |
| Tryptone-yeast-extract broth | Negative |
| Carrot plug | Abundant growth, pale yellow; no aerial mycelium |
| Potato plug | Abundant growth, grayish white; no aerial mycelium; no change in plug. |
| Temperature requirements (ISP medium No. 2 yeast extract malt extract slants) | 25° C.-Abundant growth; fair aerial mycelium; reverse light brown; no soluble pigment. |
| | 30° C.-Abundant growth; fair aerial mycelium; reverse light brown; no soluble pigment. |
| | 37° C.-Abundant growth; fair aerial mycelium; reverse-brown; soluble pigment brown. |
| | 40° C.-Abundant growth; sparse aerial mycelium; reverse red brown; soluble pigment deep red brown. |
| | 45° C.-Fair growth; no aerial mycelium; reverse red brown; moderate red brown pigment. |

The results of carbon utilization tests carried out with organism NRRL 8092 are set forth below. The symbols used to indicate growth response are:

+ good growth, positive utilization
(+) poor to fair growth
(−) faint growth, probably no utilization
− no growth, no utilization

| Carbon Source | Response |
| --- | --- |
| D-glucose | + |
| L-arabinose | + |
| D-xylose | + |
| D-fructose | + |
| sucrose | − |
| D-mannitol | − |
| i-inositol | + |
| rhamnose | + |
| raffinose | − |
| −C control (no carbohydrate) | − |

Certain characteristics of the A-28086-producing *S. aureofaciens* strains differ from the characteristics of the organism described by Shirling and Gottlieb. These differences are summarized in Table III:

Table III

| Carbon Utilization | NRRL 5758 | NRRL 8092 | Published Description |
| --- | --- | --- | --- |
| sucrose | − | − | + |
| i-inositol | + | + | − |
| rhamnose | + | + | − |
| Gelatin Liquifaction | 30% in 14 days | 50% in 14 days | Limited or none |
| Action on Milk | Milk peptonized, white growth ring | Milk peptonized, pale-yellow growth ring | Limited and variable peptonization (often none); limited growth and coagulation |

The characteristics of organism NRRL 5758 which differ from the characteristics of organism NRRL 8092 are summarized in Table IV.

Table IV

| Characteristic | NRRL 5758 | NRRL 8092 |
| --- | --- | --- |
| Vegetative Color | Yellow on several media | Cream to pale-yellow on several media |
| Sporulation | Some spiral sporophores on tomato-paste: oatmeal and inorganic salts-starch media | Short straight sporophores with occasional hooks |
| Growth on: | | |
| Calcium maleate | Growth fair, brown; with clearing | Growth sparse, clear; no clearing |
| Inorganic salts- | Moderate sporulation; aerial purplish white to gray. | Scant sporulation; aerial white |
| Bennett's agar | Reverse pale-yellow | Reverse pink |

The *Streptomyces aureofaciens* culture especially useful for the production of antibiotic A-28086 factor D has been deposited and made a part of the stock culture collection of the Northern Marketing and Nutrition Research Division, U.S. Dept. of Agriculture, Agricultural Research Service, Peoria, Ill., 61604, from which it is available to the public under the number NRRL 8092.

The culture medium employed to grow *Streptomyces aureofaciens* NRRL 8092 can be any one of a number of media. For economy in production, optimal yield, and ease of product isolation, however, certain culture media are preferred. Thus, for example, preferred carbohydrate sources in large-scale fermentation are tapioca dextrin and sucrose, although glucose, corn starch, fructose, mannose, maltose, lactose, and the like can also be employed. Corn oil, peanut oil, soybean oil and fish oil are other useful sources of carbon. A preferred nitrogen source is enzyme-hydrolyzed casein, although peptones, soybean meal, cotton-seed meal, amino acids such as glutamic acid, and the like are also useful. Among the nutrient inorganic salts which can be incorporated in the culture media are the customary soluble salts capable of yielding sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (i.e. 0.2 ml/l.) of an antifoam agent such as polypropylene glycol to large-scale fermentation media if foaming becomes a problem.

Although it is not essential, the antibiotic production of *Streptomyces aureofaciens* NRRL 8092 is enhanced by the addition of a small amount of oil such as soybean oil.

For production of substantial quantities of antibiotic A-28086 factor D, submerged aerobic fermentation in tanks is preferred. Small quantities of A-28086 factor D may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the growth of the vegetative inoculum can be the same as that employed for larger fermentations, but other media can also be employed.

The A-28086 factor D-producing organism can be grown at temperatures between about 20° and about 45° C. Optimum A-28086-factor D production appears to occur at temperatures of about 27°-30° C.

As is customary in aerobic submerged culture processes, sterile air is blown through the culture medium. For efficient growth of the organism the volume of air employed in the tank production is preferably above 0.1 volume of air per volume of culture medium per minute. For efficient production of A-28086 factor D, the volume of air employed in the tank production is preferably above 0.25 volume of air per volume of culture medium per minute. High levels of dissolved oxygen do not repress antibiotic production.

The production of A-28086 antibiotics, including factor D, can be followed during the fermentation by testing samples of the broth or of extracts of the mycelial solids for antibiotic activity against organisms known to be sensitive to the A-28086 antibiotics. One assay organism useful in testing the A-28086 antibiotics, including A-28086 factor D of the present invention, is *Bacillus subtilis* ATCC 6633. The bioassay is conveniently performed by paper-disc assay on agar plates.

The initial pH of the uninoculated culture medium varies with the medium used. In general, the pH should be in the range of 6.0 to 7.5. The harvest pH at the end of the fermentation is usually slightly higher, in the range of 6.5 to 8.0.

Generally, antibiotic activity is detectable on the second day of the fermentation. Maximum production of antibiotic A-28086 factor D usually occurs between about the eighth and the tenth days.

Following its production under submerged aerobic fermentation conditions, antibiotic A-28086 factor D is recovered, together with the co-produced A-28086 factors A and B, by methods commonly employed in the fermentation art.

The co-produced A-28086 antibiotic factors are found in both the mycelial mass and in the filtered or centrifuged fermentation broth. Maximum recovery of the A-28086 antibiotic factors is accomplished, therefore, by a combination of methods, including filtration, extraction, and adsorption chromatography. A preferred solvent for separating the co-produced A-28086 antibiotic factors from either whole or filtered fermentation broth is ethyl acetate, although other commonly used solvents are satisfactory.

An especially advantageous method of separating A-28086 factors A, B, and D is to lower the pH of the whole fermentation broth to about pH 3.0. This method is the subject of a copending application of Boeck and Berg titled ANTIBIOTIC RECOVERY PROCESS, Ser. No. 569,712, filed Apr. 21, 1975. At about pH 3.0 the A-28086 factors A, B, and D are conveniently separated with the mycelial mass by filtration. Methanol is a preferred solvent for separating the antibiotics from the mycelial mass, but other lower alcohols and ketones are also suitable.

Azeotropic distillation can also be advantageously employed in the recovery of the A-28086 antibiotic factors. In this method an organic solvent which forms an appropriate azeotrope with water is added to the aqueous fermentation broth. This solvent-broth mixture is subjected to azeotropic distillation in order to remove at least half the water from the broth, leaving a water-solvent mixture in which the A-28086 antibiotic factors are in solution in the organic solvent. Insoluble by-products can be separated by suitable means such as filtration or centrifugation. The A-28086 antibiotic factors can then be recovered from the organic solution by well-known procedures such as evaporation of solvent, precipitation by adding a nonsolvent, or extraction.

Organic solvents which form appropriate azeotropes with water in order to carry out such a recovery procedure include, illustratively, butyl alcohol, amyl alcohol, hexyl alcohol, benzyl alcohol, butyl acetate, amyl acetate, 1,2-dichloroethane, 3-pentanone, 2-hexanone, benzene, cyclohexanone, toluene, the xylenes and the like.

There is special advantage in recovery by azeotropic distillation on large-scale fermentation processes. Both water and solvent taken overhead in the azeotrope can be separated by known techniques and thereafter recycled for further use. The water thus removed is free of contaminants and does not require a waste disposal process. The solvent thus removed may be recycled to the process.

Further purification of the A-28086 antibiotic factors and separation of individual factors includes additional extraction and adsorption procedures. Adsorptive materials such as silica gel, carbon, Florisil ® (magnesium silicate, Floridin Co., P.O. Box 989, Tallahassee, Fla.) and the like can be advantageously employed.

Alternatively, the culture solids, including medium constituents and mycelium can be used without extraction or separation, but preferably after removal of water, as a source of the A-28086 antibiotic factors. For example, after production of the A-28086 antibiotic factors, the culture medium can be dried by lyophilization and mixed directly into feed premix.

In another aspect, after production of the A-28086 antibiotic factors in the culture medium, the mycelium can be separated and dried to give a product which can be used directly in a feed premix.

Under the conditions employed thus far, the new *Streptomyces aureofaciens* strain described previously and designated as NRRL 8092 produces antibiotic factor A as the major factor. Although the ratio of factors varies depending on the fermentation conditions used, in general factor A accounts for at least about 90% of the total recovered antibiotic activity. Factor D accounts for about 8-10% of the remaining activity. Factors A and D are recovered both from filtered broth and from the mycelium. Minor factor B, which accounts for substantially the remainder of the antibiotic activity, is present in amounts of less than about 1% and has thus far been observed only in the mycelium.

Another substance, arbitrarily designated as A-28086-I, is co-produced with antibiotic A-28086 factors A, B, and D. Although A-28086-I is not microbiologically active, it is structurally related to the A-28086 antibiotic factors. A-28086-I is a white crystalline compound (from acetone-water) and has a melting point of about 160°-162° C. Comparative studies of the NMR spectra and other properties of A-28086-I and synthetically-prepared A-28086 factor A methyl ester give evidence that A-28086-I is the methyl ester of A-28086 factor A or a closely related compound such as a stereoisomer.

Although A-28086-I initially co-precipitates with the active A-28086 antibiotic factors A, B, and D, it is readily separated from them by silica gel chromatography. A-28086-I has an approximate $R_f$ value of 0.53 on silica gel thin-layer chromatography with ethyl acetate as the eluting solvent and using vanillin spray reagent (3% vanillin in methanol + 0.5 ml. conc. $H_2SO_4$ per 100 ml. of solution) for detection. After spraying with vanillin and heating, A-28086-I gives a blue spot while the A-28086 antibiotic factors A, B, and D give bright pink spots which quickly turn dark.

Antibiotic A-28086 factors A, B, and D are separated from each other and are isolated as individual compounds by the use of well-known methods such as column chromatography, thin-layer chromatography and the like. For example, column chromatography over silica gel is used to separate factors A, B, and D by eluting the column with varying solvent mixtures, such as benzene-ethyl acetate. Using benzene-ethyl acetate solvent mixtures over a silica gel column, A-28086-I is eluted first; factor B is eluted next; and factors A and D are eluted together later. Additional chromatography using fine-mesh silica gel effects a separation of factors A and D. Thin-layer chromatography, as described hereinabove, is a convenient method for monitoring elution progress.

As is the case with A-28086 factors A and B, the newly-discovered A-28086-factor-D compounds of this invention also inhibit the growth of bacteria and fungi which are pathogenic to animal and plant life. One measure of the antimicrobial activity of A-28086 factor D was made using the conventional disc-diffusion method (6-mm pads were dipped in solutions containing 1 mg. of A-28086 factor D per ml. of solution; pads were placed on agar plates seeded with test organism). The results of these tests are summarized in Table V.

TABLE V

| Test Organism | Zone of Inhibition (mm) |
|---|---|
| Staphylococcus aureus | 22 |
| Bacillus subtilis ATCC6633 | 31 |
| Sarcina lutea ATCC9341 | 26 |
| Saccharomyces pastorianum ATCC2366 | 20 |
| Neurospora crassa. | 12 |
| Candida albicans | 19 |

In another aspect of their antimicrobial activity, A-28086-factor-D compounds inhibit the growth of anaerobic bacteria. The minimal inhibitory concentrations (MIC's) at which A-28086 factor D inhibits various anaerobic bacteria were determined by standard agar-dilution assay. Endpoints were read after 24-hour incubation. The results of these tests are summarized in Table VI.

TABLE VI

| Test Organism | MIC (µg/ml) |
|---|---|
| Actinomyces bovis | <0.5 |
| Clostridium inocuum | <0.5 |
| Clostridium perfringens | <0.5 |
| Clostridium ramosum | <0.5 |
| Clostridium septicum | <0.5 |
| Clostridium septicum bovine | <0.5 |
| Eubacterium aerofaciens | <0.5 |
| Peptococcus anaerobius | <0.5 |
| Peptostreptococcus intermedius | <0.5 |
| Propionibacterium acnes 44 | <0.5 |
| Propionibacterium acnes 79 | <0.5 |
| Bacteroides fragilis ssp. fragilis 1877 | 4.0 |
| Bacteroides fragilis ssp. fragilis 1936B | 8.0 |
| Bacteroides fragilis ssp. | |

TABLE VI-continued

| Test Organism | MIC (μg/ml) |
|---|---|
| thetaiotaomicron | 4.0 |
| Bacteroides fragilis ssp. vulgatis No. 1563 | 4.0 |
| Bacteroides fragilis ssp. vulgatis 1211 | 4.0 |
| Fusobacterium symbiosum | 2.0 |
| Fusobacterium necrophorum | 16.0 |
| Veillonella alcalescens | 2.0 |

The A-28086-factor-D-compounds are also antiviral agents. A-28086 factor D is active against Maryland B agents, type III poliovirus, COE virus, herpes virus and Semliki Forest virus, as demonstrated by in vitro plaque suppression tests, similar to that described by Siminoff, Applied Microbiology 9 [1], 66–72 (1961). A-28086 factor D, is also active against Transmissible Gastro-enteritis virus, Newcastle Disease virus, and Infectious Bovine Rhinotracheitis virus, as demonstrated by similar tissue-culture tests.

The fact that the A-28086-factor-D compounds have activity both against viruses and against anaerobic bacteria makes these compounds particularly beneficial for the treatment or prevention of enteritis in chickens, swine, cattle and sheep. The A-28086-factor-D compounds are also useful for the treatment of entero-toxemia in ruminants.

Anticoccidial activity is an important property of the A-28086-factor-D compounds of this invention. Experiments in vitro demonstrate the anticoccidial activity of A-28086 factor D against *Eimeria tenella*. The following method was used [for further details, see L. R. McDougald and R. B. Galloway in *Exper. Parasitology* 34, 189–196 (1973)]:

Host cell cultures are prepared by conventional techniques using Leighton tubes, plastic dishes or plates, or other suitable culture vessels. Following 2-3 days growth in any suitable culture medium (Eagle's minimal essential medium, lactalbumin hydrolysate in Earle's or Hank's balanced saline, Medium 199, etc.) a suitable monolayer usually forms and is ready for infection and drug treatment. Primary cultures of chick kidney cells were used for these studies.

Viable oocysts of *Eimeria tenella* are obtained from the feces of infected chickens and are cleaned and sterilized prior to use. The oocysts are sporulated by incubation at room temperature while bubbling air through the suspension or by shaking gently on a gyrotory shaker or by other suitable means. Potassium dichromate or sulfuric acid (or other chemicals) may be employed to prevent bacterial or mold growth during sporulation.

Excystation of infective sporozoites from the oocysts is accomplished by a combination of mechanical disruption of the oocyst wall, followed by treatment with trypsin and bile salts to induce the sporozoites to free themselves from the sporocysts.

Cell cultures are infected by the introduction of viable sporozoites into the culture vessel. Test chemicals can be introduced at this time or subsequently. The test chemical is introduced in the desired concentration in 10% dimethylformamide in physiological saline. The endpoint of the test is inhibition of asexual developmental stages, and is determined by microscopic examination of cultures fixed and stained 96 hrs. postinfection. Results are recorded as active (A), inactive (N) or cytotoxic (C) depending on the presence or absence of second-generation schizonts and any apparent toxicity to the cell monolayer.

The anticoccidial activity of A-28086 factor D demonstrated by this test is summarized in Table VII

TABLE VII

Anticoccidial Activity of Antibiotic A-28086 Factor D

| Concentration of A-28086 Factor D (mcg/ml) | Rating |
|---|---|
| 5 | C |
| 1 | C |
| 0.2 | C |
| 0.4 | A,C* |
| 0.03 | A |
| 0.02 | A |
| 0.01 | ± A |
| 0.008 | N |

*Results of two tests

Another useful feature of the A-28086-factor-D compounds is their ability to improve feed-utilization efficiency in ruminant animals which have a developed rumen function. The mechanism for utilization of the major nutritive portion (carbohydrates) of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids (VFA). For a more detailed discussion, see Leng in "Physiology of Digestion and Metabolism in the Ruminant," Phillipson et al., Eds., Oriel Press, Newcastle upon Tyne, England, 1970, pp 408–410.

The relative efficiency of VFA utilization is discussed by McCullough in *Feedstuffs*, June 19, 1971, page 19; Eskeland et al. in *J. An. Sci.* 33, 282 (1971); and Church et al. in "Digestive Physiology and Nutrition of Ruminants," Vol. 2, 1971, pp 622 and 625. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate-utilization efficiency and also reducing the incidence of ketosis.

The activity of such a beneficial compound can be determined by observing its effect on the production and concentration of propionate compounds in the rumen, using the following methods:

Rumen fluid is obtained from a steer with a surgically-installed fistula opening into the rumen. The steer is maintained on a high-grain ration. A sample of rumen fluid is strained through four layers of cheesecloth, and the filtrate is collected. The particulate matter retained by the cheesecloth is resuspended in enough physiological buffer to return it to the original volume of the rumen fluid, and this suspension is strained again. The buffer used has the following composition:

| Ingredient | g/liter |
|---|---|
| $Na_2HPO_4$ | 0.316 |
| $KH_2PO_4$ | 0.152 |
| $NaHCO_3$ | 2.260 |
| KCl | 0.375 |
| NaCl | 0.375 |
| $MgSO_4$ | 0.112 |
| $CaCl_2 \cdot 2H_2O$ | 0.050 |
| $FeSO_4 \cdot 7H_2O$ | 0.008 |
| $MnSO_4 \cdot H_2O$ | 0.004 |
| $ZnSO_4 \cdot 7H_2O$ | 0.004 |
| $CuSO_4 \cdot 5H_2O$ | 0.002 |

| Ingredient | g/liter |
| --- | --- |
| CoCl$_2$ · 6H$_2$O | 0.001 | as described by Cheng et al. in *J. Dairy Sci.* 38, 1225–1230 (1955).

The two filtrates are combined and allowed to stand until particulate matter separates to the top. The clear layer is separated, diluted with the same buffer (1:1) and then adjusted to between pH 6.8 to 7.0.

The diluted rumen fluid (10 ml.) is placed in a 25-ml. flask with 40 mg. of the above-described feed, an additional 1 mg. of soybean protein, and the compound to be tested. Four replicate flasks are used per treatment. Two sets of four control flasks each are also employed. A zero-time control and an incubated 16-hour control are used. All test flasks are incubated for 16 hours at 38° C. After incubation the pH is meaured, and 25 percent metaphosphoric acid (2 ml.) is added to each flask. The samples are allowed to settle, and the supernatants are analyzed by gas chromatography for propionate, acetate, and butyrate compounds. Active compounds significantly increase propionate production over that of controls.

Test-compound results are statistically compared with control results. Table VIII shows the ratio of volatile-fatty-acid concentrations in A-28086-factor-D-treated flasks to concentrations in control flasks.

TABLE VIII

| A-28086 D mcg/ml. | Molar % Acetate | Molar % Butyrate | Molar % Propionate | Total VFA mM/l |
| --- | --- | --- | --- | --- |
| 1.0 | 0.8715 | 0.7973 | 1.7981 | 1.1979 |
| 0.3 | 0.8976 | 0.8726 | 1.5871 | 1.0630 |

The A-28086-factor-D compounds of this invention are typically effective in increasing the efficiency of feed-utilization when administered to ruminants orally at rates of from about 0.05 mg./kg./day to about 5.0 mg./kg./day. Most beneficial results are achieved at rates of from about 0.1 mg./kg./day to about 2.5 mg./kg./day. A preferred method of administration of an A-28086-factor-D compound is by mixing it with the animals' feed; however, it can be administered in other ways, for example, tablets, drenches, boluses, or capsules. Formulation of these various dosage forms can be accomplished by methods well known in the veterinary pharmaceutical art. Each individual dosage unit should contain a quantity of an A-28086-factor-D compound directly related to the proper daily dose for the animal to be treated.

This invention further relates to feed compositions adapted to fatten cattle comprising cattle feed and from 1 to 30 grams per ton of an A-28086-factor-D compound.

In order to illustrate more fully the operation of this invention, the following examples are provided.

EXAMPLE 1

A. Shake-flask Fermentation of A-28086

A culture of *Streptomyces aureofaciens* NRRL 8092 was prepared and maintained on an agar slant having the following composition:

| Ingredient | Amount |
| --- | --- |
| K$_2$HPO$_4$ | 2 g. |
| MgSO$_4$ · 7H$_2$O | 0.25 g. |
| NH$_4$NO$_3$ | 2 g. |
| CaCO$_3$ | 2.5 g. |
| FeSO$_4$ · 7H$_2$O | 0.001 g. |
| MnCl$_2$ · 7H$_2$O | 0.001 g. |
| ZnSO$_4$ · 7H$_2$O | 0.001 g. |
| Glucose | 10 g. |
| Agar | 20 g. |
| Deionized water-q.s. | 1 liter |
| pH (unadjusted) | 7.7 |

The slant was inoculated with *Streptomyces aureofaciens* NRRL 8092, and the inoculated slant was incubated at 30° C. for about 7 days. The mature slant culture was covered with sterile beef serum and was scraped with a sterile loop to prepare a spore and mycelial suspension from the slant culture. The resulting suspension was lyophilized into a maximum of six pellets.

One of the lyophile pellets thus prepared was used to inoculate 50 ml. of a vegetative medium having the following composition:

| Ingredient | Amount |
| --- | --- |
| Glucose | 20 g. |
| Soybean flour | 15 g. |
| Corn steep liquor | 10 g. |
| CaCO$_3$ | 2 g. |
| Tap water q.s. | 1 liter |
| pH adjusted to pH 6.5 with dil NaOH | |

The inoculated vegetative medium, in a 250-ml. Erlenmeyer flask, was incubated at 30° C. for 48 hours on a rotary shaker at 250 rpm with a 2-inch arc.

This incubated vegetative medium described above (0.5 ml., 1 percent) was used to inoculate 50 ml. of a fermentation medium having the following composition:

| Ingredient | Amount |
| --- | --- |
| Tapioca dextrin* | 60.0 g. |
| Enzyme-hydrolyzed casein** | 6.0 g. |
| Enzymatic hydrolysate of casein*** | 2.0 g. |
| CaCO$_3$ | 2.0 g. |
| MgSO$_4$ · 7H$_2$O | 0.5 g. |
| Blackstrap molasses | 15.0 g. |
| Refined soybean oil | 5.0 ml. |
| Tap water q.s. | 1 liter |
| pH (unadjusted) | 6.6 |

*Staley Dextrin No. 11, A.E. Staley Co., Decatur, Ill.
**Amber EHC, Amber Laboratories, Juneau, Wisc.
***NZ Amine A, Sheffield Chemical Co., Norwich, N.Y.

B. Tank Fermentation of A-28086

The initial procedure described in (A) for the shake-flask fermentation of A-28086 was also used for tank fermentation. In order to produce a larger volume of inoculum, 10 ml. of the incubated vegetative medium was used to inoculate 400 ml. of a second-stage vegetative medium having the same composition as that of the vegetative medium. This second-stage medium, in a 2-liter Erlenmeyer flask, was incubated at 30° C. for 24 hours on a rotary shaker at 250 rpm with a 2-inch arc.

This incubated second-stage vegetative medium (800 ml.) was used to inoculate 100 liters of sterile fermentation medium having the following composition:

| Ingredient | Amount |
| --- | --- |
| Tapioca dextrin* | 60.0 g/l. |

-continued

| Ingredient | Amount |
| --- | --- |
| Enzyme-hydrolyzed casein** | 6.0 g/l. |
| Enzymatic-hydrolysate of casein*** | 2.0 g/l. |
| $CaCO_3$ | 2.0 g/l. |
| $MgSO_4 \cdot 7H_2O$ | 0.5 g/l. |
| Blackstrap molasses | 15.0 g/l. |
| Refined soybean oil | 5.0 ml/l. |
| Tap water q.s. | 1 liter |

*Staley Dextrin No. 11, A.E. Staley Co., Decatur, Ill.
**Amber EHC, Amber Laboratories, Juneau, Wisc.
***NZ Amine A, Sheffield Chemical Co., Norwich, N.Y.

The pH of the medium was 6.8 ± 0.1 after sterilization by autoclaving at 121° C. for 30 minutes at 15–20 pounds pressure. In a 165-liter fermentation tank, the inoculated production medium was allowed to ferment for 10–12 days at 28° ± 1° C. The fermentation medium was aerated with sterile air at the rate of 0.4 volumes of air per volume of culture medium per minute. The medium was stirred with conventional agitators at 300 rpm.

EXAMPLE 2

The A-28086 antibiotics were produced according to the process of Example 1, but using a shake-flask/tank production medium having the following composition:

| Ingredient | Amount |
| --- | --- |
| Tapioca dextrin* | 30.0 g/l. |
| Glucose | 15.0 g/l. |
| Enzyme-hydrolyzed casein** | 3.0 g/l. |
| Enzymatic-hydrolysate of casein*** | 1.0 g/l. |
| Yeast extract | 2.5 g/l. |
| $CaCO_3$ | 2.0 g/l. |
| $MgSO_4 \cdot 7H_2O$ | 1.0 g/l. |
| Blackstrap molasses | 15.0 g/l. |
| Refined soybean oil | 5.0 ml/l. |
| Tap water q.s. | 1 liter |

*Staley Dextrin No. 11, A.E. Staley Co., Decatur, Ill.
**Amber EHC, Amber Laboratories, Juneau, Wisc.
***NZ Amine A, Sheffield Chemical Co., Norwich, N.Y.

The pH of the medium was 6.4 after sterilization by autoclaving as described in Example 1.

EXAMPLE 3

Separation of the A-28086 Factors A, B, and D

Whole fermentation broth (60 liters), obtained by the method described in Example 1, was adjusted to pH 3 by the addition of dilute HCl. The resulting solution was filtered using a filter aid (Hyflo Super-cel, a diatomaceous earth, Johns-Manville Products Corp.). The separated mycelial cake was extracted with 30 liters of methanol, adding 1.56 kg. of $NaHCO_3$ to the extract with stirring. After separation of this extract, the mycelial cake was again extracted with another 30 liters of methanol. The two methanol extracts were combined and concentrated under vacuum to remove the methanol. The remaining aqueous solution (about 7 liters) was adjusted to pH 7.5 with dilute HCl. The resulting solution was extracted twice with ethyl acetate (7-liter portions). The ethyl acetate extracts were combined and concentrated under vacuum to give an oily residue. This oily residue was dissolved in 1500 ml. of acetone. Water (1500 ml.) was added to the acetone solution. The resulting solution was adjusted to pH 3 with dilute HCl and was stirred one hour. The precipitate which had formed was separated by filtration and then was dissolved in acetone (1500 ml.); water (400 ml.) was added to this solution. The resulting solution was allowed to stand for 16 hours for crystallization to occur. The crystals formed were separated by filtration and dried under vacuum to give 74 g. crude crystalline product containing A-28086 factors D and A and other crystalline impurities.

This crude crystalline product (40 g.) was dissolved in about 250 ml. of benzene. The benzene solution was then applied to a silica gel column (9- × 120-cm column; Grace-Davidson grade 62 silica gel). The column was eluted successively with 40 liters of each of the following:

(1) benzene
(2) benzene: ethyl acetate (9:1)
(3) benzene: ethyl acetate (4:1)
(4) benzene: ethyl acetate (7:3)
(5) benzene: ethyl acetate (1:1)
(6) ethyl acetate
(7) methanol One-liter fractions were collected. Each fraction was checked by assay against *Bacillus subtilis* and by thin-layer chromatography to identify the eluted compounds. A-28086-I was eluted with benzene:ethyl acetate (4:1). A-28086 factor B was separated during elution with benzene: ethyl acetate (7:3). A-28086 factors A and D were eluted in the fractions obtained with benzene: ethyl acetate (7:3 and 1:1), fractions 119–156. These fractions were combined and evaporated to dryness under vacuum. The residue thus obtained was dissolved in acetone (500 ml.). Water (500 ml.) was added to the acetone solution, and the resulting solution was adjusted to pH 3 with dilute HCl and was stirred for one hour. The precipitate which formed was separated by filtration and was crystallized from acetone (500 ml.)-water (180 ml.). The crystals thus formed were separated by filtration and dried under vauum to give 20.1 g. of a mixture of A-28086 factors A and D.

EXAMPLE 4

Separation and Purification of Individual Factors A and D

The crystalline mixture of A-28086 factors A and D obtained in Example 3 (18.8 g.) was dissolved in benzene (50 ml). The benzene solution was applied to a silica-gel column (7- × 100-cm column; E. Merck grade 60 silica gel, finer than 230 mesh ASTM). The column was eluted, at a flow rate of 90 ml. per hour, successively with:

(1) 12 liters of benzene
(2) 12 liters of benzene:ethyl acetate (9:1)
(3) 12 liters of benzene:ethyl acetate (4:1)
(4) 32 liters of benzene:ethyl acetate (7:3)
(5) 10 liters of methanol Thin-layer cellulose chromatography (Merck Darmstadt cellulose on aluminum support) was followed by *B. subtilis* bioautography to monitor the elution procedure. The following solvent system was used: water:methanol:acetone (12:3:1), adjusting the solution first to pH 10.5 with $NH_4OH$ and then to pH 7.5 with HCl.

One- to 2-liter fractions were collected until activity was detected; then 200-ml. fractions were collected. The fractions containing only A-28086 factor D were combined and evaporated under vacuum to a residue. This residue was crystallized from acetone-water (1:1). The crystals were separated and dried under vacuum to give 140 mg. of crystalline A-28086 factor D.

The fractions containing A-28086 factor D with a trace of A-28086 factor A were treated in the same manner to give an additional 150 mg. of crystalline A-28086 factor D containing a small amount of A-28086 factor A.

The fractions containing only A-28086 factor A were also treated in the same manner to give 4.7 g. of crystalline A-28086 factor A.

EXAMPLE 5

A-28086 Factor D Acetyl Ester Derivative

Antibiotic A-28086 factor D (28.1 mg) was dissolved in pyridine (2 ml). Acetic anhydride (2 ml) was added to this solution. The resulting solution was mixed thoroughly and then was allowed to stand overnight at room temperature.

An excess of water (5 ml) was then added, mixing thoroughly and allowing the mixture to stand for several hours at room temperature. The precipitate which formed was separated by filtration, washed with water, and dried to give 17.8 mg of A-28086 factor D acetyl ester derivative (63.3% yield).

EXAMPLES 6-9

Antibiotic A-28086 factor D propionyl ester derivative, prepared by reacting A-28086 factor D with propionic anhydride in the presence of pyridine according to the method of Example 5.

Antibiotic A-28086 factor D n-butyryl ester derivative was prepared by reacting A-28086 factor D (29.5 mg) with n-butyric anhydride (2 ml) in the presence of pyridine (2 ml) according to the method of Example 5. After the excess of water (5 ml) was added and the mixture was allowed to stand, the solution was concentrated under vacuum to a volume of about 2 ml. To this concentration, acetone (2 ml) was added. Water (approx. 4 ml) was added dropwise to the solution until turbidity was apparent. The mixture was allowed to stand at room temperature about an hour and then was refrigerated several hours until a precipitate had formed. This precipitate was separated by filtration and then was dissolved in dioxane. The dioxane solution was evaporated to dryness under vacuum to give 16.4 mg. of A-28086 factor D n-butyryl ester derivative (55.6% yield).

Antibiotic A-28086 factor D n-caproyl ester derivative, prepared by reacting A-28086 factor D with caproic anhydride in the presence of pyridine according to the method of Example 5.

Antibiotic A-28086 factor D n-valeryl ester derivative, prepared by reacting A-28086 factor D with valeric anhydride in the presence of pyridine according to the method of Example 5.

EXAMPLE 10

Preparation of A-28086 Factor D Sodium Salt

Antibiotic A-28086 factor D is dissolved in acetone. An equivalent amount of water is added to this solution, and sufficient 5 N sodium hydroxide is added to bring the pH of the solution to about pH 11. The resulting solution is stirred for about an hour and then is extracted with ethyl acetate. The ethyl acetate extract is evaporated under vacuum to give A-28086 factor D sodium salt.

EXAMPLES 11-13

Antibiotic A-28086 factor D potassium salt, prepared from A-28086 factor D and 5 N potassium hydroxide, using the method of Example 10.

Antibiotic A-28086 factor D barium salt, prepared from A-28086 factor D and saturated barium hydroxide, using the method of Example 10.

Antibiotic A-28086 factor D cesium salt, prepared from A-28086 factor D and 1 N cesium hydroxide, using the method of Example 10.

EXAMPLE 14

Chick Ration Containing A-28086 Factor D for Coccidiosis Control

A balanced, high-energy ration adapted to feed chicks for rapid weight gain is prepared by the following recipe:

| Ingredient | % | lbs |
|---|---|---|
| Ground yellow corn | 50 | 1,000 |
| Soybean meal, solvent-extracted dehulled, finely ground, 50 percent protein | 31.09 | 621.8 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A, D, E, K, and $B_{12}$, choline, niacin, pantothenic acid, riboflavin, biotin, with glucose bulking agent) | 0.5 | 10 |
| Trace mineral premix (representing $MnSO_4$, ZnO, KI, $FeSO_4$, $CaCO_3$) | 0.2 | 4 |
| 2-Amino-4-hydroxybutyric acid (hydroxy analog of methionine) | 0.1 | 2 |
| A-28086 Factor D | 0.01 | 0.2 |

These substances are mixed in accordance with standard free-mixing techniques. Chicks fed such a ration, with water ad libitum, are protected against exposure to coccidiosis; weight gains are comparable to those of coccidiosis-free chicks fed a similar, unmedicated diet.

EXAMPLE 15

Beef-Cattle Ration Containing A-28086 Factor D

A balanced high-grain beef-cattle ration is prepared as follows:

| Ingredient | % | lbs |
|---|---|---|
| Finely ground corn | 67.8 | 1356 |
| Ground corn cob | 10 | 200 |
| Dehydrated alfalfa meal, 17 percent protein | 5 | 100 |
| Dehulled soybean meal, solvent extracted, 50 percent protein | 9.9956 | 199.912 |
| Cane molasses | 5 | 100.0 |
| Urea | 0.6 | 12.0 |
| A-28086 Factor D | 0.0044 | 0.088 |
| Dicalcium phosphate, feed grade | 0.5 | 10.0 |
| Calcium carbonate | 0.5 | 10.0 |
| Sodium chloride | 0.3 | 6.0 |
| Trace mineral premix | 0.03 | 0.6 |
| Vitamin A and $D_2$ premix* | 0.07 | 1.4 |

-continued

| Ingredient | % | lbs |
|---|---|---|
| Vitamin E premix** | 0.05 | 1.0 |
| Calcium propionate | 0.15 | 3.0 |

*Containing per pound: 2,000,000 I.U. of vitamin A; 227,200 I.U. of vitamin $D_2$ and 385.7 g. of soybean feed with 1% oil added
**Corn distillers dried grains with solubles containing 20,000 I.U. of d-alpha-tocopheryl acetate per pound The mixed feed was compressed into pellets. At an average daily ingestion rate of 15 pounds of feed per animal, this feed supplies approximately 300 mg. of A-28086 factor D per animal per day.

We claim:

1. A method of preventing or treating coccidiosis in poultry which comprises administering to poultry an effective anticoccidial amount of a composition comprising: (1) a compound selected from the group consisting of antibiotic A-28086 factor D which is a white crystalline compound when crystallized from acetone-water; which is soluble in methanol, ethanol, dimethylformamide, dimethyl sulfoxide, ethyl acetate, chloroform, acetone and benzene; but which is only slightly soluble in hexane; and which is insoluble in water; which melts at about 96°–98° C., and which has:

(a) a molecular weight of 778, as determined by high-resolution mass spectrometry;

(b) an approximate elemental composition of 67.59 percent carbon; 9.38 percent hydrogen, and 22.77 percent oxygen;

(c) an empirical formula of $C_{44}H_{74}O_{11}$, as determined by high-resolution mass spectrometry;

(d) a specific rotation of $-56°$ ($c = 0.1$, methanol) when determined at 25° C.;

(e) an infrared absorption spectrum in chloroform with the following observable absorption maxima: 2.89, 3.39, 3.43, 3.50, 5.88, 6.90, 7.27, 7.60, 7.84, 9.00, 9.26, 9.62, 10.31, 10.58, 11.10, and 11.49 microns;

(f) no observable ultraviolet absorption in 95 percent aqueous ethanol;

(g) a nuclear magnetic resonance spectrum in chloroform with the following characteristics: $\delta$ 6.00, 4.20, 4.10, 4.00, 3.98, 3.92, 3.86, 3.83, 3.79, 3.67, 3.64, 3.57, 3.54, 2.88, 2.81, 2.71, 2.62, 2.58, 2.48, 2.43, 2.37, 2.29, 2.21, 2.15, 2.10, 2.04, 1.97, 1.89, 1.83, 1.76, 1.68, 1.61, 1.58, 1.55, 1.47, 1.39, 1.30, 1.25, 1.18, 0.95, 0.90, 0.88, 0.84, 0.74, and 0.68 ppm;

(h) a titratable group with a $pK_a$ value of 8.67 in 80% aqueous dimethylformamide;

(i) a characteristic X-ray powder-diffraction pattern ($Cu^{++}$ radiation, 1.5405 $\lambda$, nickel filter) having the following interplanar spacings in angströms (d):

| d | Relative Intensity |
|---|---|
| 12.40 | 100 |
| 10.20 | 70 |
| 8.85 | 90 |
| 7.80 | 30 |
| 6.80 | 10 |
| 6.30 | 100 |
| 5.70 | 20 |
| 5.35 | 20 |
| 5.10 | 20 |
| 4.90 | 10 |
| 4.65 | 20 |
| 4.45 | 40 |
| 4.20 | 30 |
| 3.30 | 10 |
| 3.15 | 10 |
| 2.99 | 05 |
| 2.77 | 05 |
| 2.28 | 05 |

(j) the following $R_f$ values in the silica-gel thin-layer chromatographic systems indicated below, using *Bacillus subtilis* ATCC 6633 as a detection organism:

| $R_f$ Value | Solvent System |
|---|---|
| 0.26 | Benzene-ethyl acetate (3:2) |
| 0.66 | Ethyl acetate-diethylamine (95:5) |

(k) the following $R_f$ values in the paper chromatographic systems indicated below, using *Bacillus subtilis* ATCC 6633 as a detection organism:

| $R_f$ Value | Solvent System |
|---|---|
| 0.10 | Water saturated with methyl isobutyl ketone (MIBK) |
| 0.26 | Water saturated with MIBK plus 2% p-toluenesulfonic acid and 1% piperidine |
| 0.36 | Water:methanol:acetone (12:3:1)-adjusted to pH 10.5 with $NH_4OH$ and then lowered to pH 7.5 with $H_3PO_4$ |
| 0.29 | 1% MIBK, 0.5% $NH_4OH$ in water |
| 0.25 | 17.4 g. $K_2HPO_4$, 30 ml. ethanol per liter of water |
| 0.26 | Benzene saturated with water |
| 0.09 | Water |
| 0.64 | Water:MIBK:ethyl acetate (98:1:1) |

(l) an acid function capable of forming salts and ester derivatives; and (m) at least one hydroxyl group capable of esterification;

the acetyl ester derivative of A-28086 factor D which has a molecular weight of about 820, as determined by electron-impact mass spectrometry, an empirical formula of $C_{46}H_{76}O_{12}$, an elemental composition of approximately 67.32 percent carbon, 9.27 percent hydrogen, and 23.41 percent oxygen, an approximate $R_f$ value of 0.54 on silica-gel thin-layer chromatography in ethyl acetate, and an infrared absorption spectrum as shown in FIG. 2 of the drawings; the n-butyryl ester derivative of A-28086 factor D which has a molecular weight of about 848, as determined by electron-impact mass spectrometry, an empirical formula of $C_{48}H_{80}O_{12}$, an elemental composition of approximately 67.93 percent carbon, 9.43 percent hydrogen, and 22.44 percent oxygen, an approximate $R_f$ value of 0.61 on silica-gel thin-layer chromatography in ethyl acetate, and an infrared absorption spectrum as shown in FIG. 3 of the drawings; the physiologically-acceptable salts of A-28086 factor D; and the physiologically-acceptable salts of the acetyl and n-butyryl ester derivatives of A-28086 factor D; and (2) a physiologically-acceptable carrier.

2. The method of claim 1 wherein the carrier is a poultry feed.

3. The method of claim 1 wherein the compound is antibiotic A-28086 factor D or a physiologically-acceptable salt of A-28086 factor D.

4. The method of claim 3 wherein the carrier is a poultry feed.

5. An anticoccidial feed composition comprising poultry feed and from 0.003 to 0.04 percent of a compound selected from the group defined in claim 1.

6. The feed composition of claim 5 wherein the compound selected is antibiotic A-28086 factor D or a physiologically-acceptable salt of A-28086 factor D.

7. A method of increasing feed-utilization efficiency in ruminant animals which comprises orally administering to said animals a propionate-increasing amount of a compound selected from the group defined in claim 1.

8. A method of claim 7 wherein the compound selected is antibiotic A-28086 factor D or a physiologically-acceptable salt of A-28086 factor D.

9. A feed adapted to fatten cattle comprising from 1 to 30 grams of a compound selected from the group defined in claim 1 per ton of cattle feed.

10. A feed of claim 9 wherein the compound selected is antibiotic A-28086 factor D or a physiologically-acceptable salt of A-28086 factor D.

* * * * *